United States Patent
Baruth et al.

(10) Patent No.: US 11,000,247 B2
(45) Date of Patent: May 11, 2021

(54) METHOD FOR OPERATING AN X-RAY DEVICE WITH ENHANCED DEPICTION OF A MEDICAL COMPONENT

(71) Applicants: Oliver Baruth, Erlangen (DE); Terrence Chen, Princeton, NJ (US)

(72) Inventors: Oliver Baruth, Erlangen (DE); Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 150 days.

(21) Appl. No.: 15/878,867

(22) Filed: Jan. 24, 2018

(65) Prior Publication Data
US 2018/0206807 A1    Jul. 26, 2018

(30) Foreign Application Priority Data
Jan. 25, 2017  (DE) .......................... 10 2017 201 162.9

(51) Int. Cl.
*A61B 6/12* (2006.01)
*A61B 6/00* (2006.01)
(Continued)

(52) U.S. Cl.
CPC .............. *A61B 6/461* (2013.01); *A61B 6/12* (2013.01); *A61B 6/469* (2013.01); *G06T 5/50* (2013.01);
(Continued)

(58) Field of Classification Search
CPC .......... A61B 6/461; A61B 6/542; A61B 6/42; A61B 6/46; A61B 6/52; H04N 5/32;
(Continued)

(56) References Cited

U.S. PATENT DOCUMENTS

| 8,311,308 B2 | 11/2012 | Chen et al. |
| 8,433,115 B2 | 4/2013 | Chen et al. |
| (Continued) | | |

FOREIGN PATENT DOCUMENTS

| EP | 1484717 A2 | 12/2004 |
| EP | 2196146 A1 | 6/2010 |

OTHER PUBLICATIONS

German Office Action for German Application No. 102017201162.9, dated Nov. 16, 2017.

*Primary Examiner* — David P Porta
*Assistant Examiner* — Mamadou Faye
(74) *Attorney, Agent, or Firm* — Lempia Summerfield Katz LLC

(57) ABSTRACT

A method is provided for operating a medical imaging X-ray device. The method records an earlier individual image of a series of images of a patient using a recording facility. The location of a medical component is identified, and the medical component is localized in the earlier individual image using a computing facility. A subregion of the earlier individual image is specified, determined by the position of the medical component localized in the earlier individual image and with the localized medical component represented. A later individual image is recorded and the medical component is localized in the later individual image. The later individual image is displayed, the later individual image averaged exclusively region-specifically in the region of the medical component with the subregion of the earlier individual image. Method acts are repeated with the displayed individual image as the earlier individual image to enhance visibility of the medical component.

10 Claims, 1 Drawing Sheet

(51) Int. Cl.
*H04N 5/32* (2006.01)
*H04N 5/232* (2006.01)
*H04N 5/272* (2006.01)
*G06T 7/11* (2017.01)
*G06T 7/70* (2017.01)
*G06T 5/50* (2006.01)

(52) U.S. Cl.
CPC .................. *G06T 7/11* (2017.01); *G06T 7/70* (2017.01); *H04N 5/23293* (2013.01); *H04N 5/232935* (2018.08); *H04N 5/232945* (2018.08); *H04N 5/272* (2013.01); *H04N 5/32* (2013.01); *G06T 2207/10016* (2013.01); *G06T 2207/10116* (2013.01); *G06T 2207/20012* (2013.01); *G06T 2207/20182* (2013.01); *G06T 2207/20216* (2013.01); *G06T 2207/30052* (2013.01); *G06T 2207/30101* (2013.01); *G06T 2207/30204* (2013.01)

(58) Field of Classification Search
CPC ........... H04N 5/321; H05G 1/60; H05G 1/28; H05G 1/38; H05G 1/40; H05G 1/42; H05G 1/44; H05G 1/46
See application file for complete search history.

(56) References Cited

U.S. PATENT DOCUMENTS

| | | | |
|---|---|---|---|
| 9,082,158 | B2 | 7/2015 | Chen et al. |
| 9,119,573 | B2 | 9/2015 | Lu et al. |
| 2005/0058363 | A1* | 3/2005 | Florent .................. G06T 5/002 382/261 |
| 2008/0267475 | A1* | 10/2008 | Lendl ...................... A61B 6/12 382/130 |
| 2013/0331687 | A1 | 12/2013 | Liao et al. |
| 2017/0154413 | A1* | 6/2017 | Yu ........................ G06K 9/6223 |
| 2017/0295300 | A1* | 10/2017 | Esashi .................... H04N 1/405 |
| 2018/0206809 | A1* | 7/2018 | Sato ........................ A61B 6/469 |

* cited by examiner

METHOD FOR OPERATING AN X-RAY DEVICE WITH ENHANCED DEPICTION OF A MEDICAL COMPONENT

CROSS-REFERENCE TO RELATED APPLICATIONS

The present patent document claims the benefit of DE 10 2017 201162.9, filed on Jan. 25, 2017, which is hereby incorporated by reference in its entirety.

BACKGROUND

With X-ray based medical imaging, the following simple relationship applies: the greater the dose invested, the better the quality of an X-ray image because there is reduced image noise with a higher dose. Numerous surgical interventions require good visibility of a medical component in a patient's body (e.g., a vessel support device, known as a stent) for successful therapy (e.g., cardiovascular therapy). Here, good visibility is characterized by high contrast, low noise and good resolution of the X-ray image. During such interventions, it is necessary to ensure that the medical component (e.g., the stent) is positioned correctly relative to other stents and/or side branches from a vessel and that the stent is correctly deployed. To verify this, it is generally also necessary to administer a contrast agent. It may also be necessary to identify any damaged elements of the medical component (e.g., a broken stent) to enable suitable measures to be taken.

The best way of enhancing the visibility of a medical component during a surgical intervention in moving body regions is to create a corresponding X-ray image in a short time and with a corresponding high dose. For example, optimally, the recording time for an X-ray image or X-ray recording during a cardiologic intervention is less than 6 milliseconds because the stent is moved by the beating of the heart. Consequently, longer recording times are associated with motion unsharpness and visibility of the stent is impaired. However, the power of X-rays is limited and it is not possible to achieve the dose required for good visibility in such short radiation pulses of less than 6 milliseconds.

One way to enhance visibility, even in this kind of situation with a moving medical component, is to identify markers (e.g., so-called balloon markers of the medical component, such as stent balloon markers) in the individual X-ray images of a series of X-ray images or a film of this kind and to register the images in the series to one another on a marker-pair basis (e.g., to assign respective image points of the images representing the same balloon markers to one another and then to average the images). For example, the registration of the individual images may take place by affine transformation. One precondition for the best way of carrying out this method is for the balloon markers to be positioned approximately at the start and end of the stent for which visibility is to be enhanced and for there to be no relative movement, or only a slight relative movement, between the markers and the medical component (e.g., the stent) during the series in the scene. The resulting image may then be further optimized with suitable image processing routines so that the medical component is visible against a smooth background. This method is known and described in numerous patents (e.g., U.S. Pat. No. 8,311,308B2 or U.S. Pat. No. 8,433,115B2) and inter alia integrated in current Siemens products as "Clear Stent" or "Clear Stent Live".

With the Clear Stent method, first, a series of images including individual images is recorded with corresponding markers and the medical component, the balloon markers and the stent. When the recording is finished, an algorithm evaluates the individual images using the method described and generates a static result image. This procedure is sometimes too slow for surgical interventions because the physician has to wait for the duration of the recording time plus the algorithm calculation time before commencing or continuing the therapy.

In the Clear Stent Live method, to speed up the method, first, a number of individual images is recorded in an initial phase 1 (e.g., over one second or 10-15 individual images). The markers are identified (e.g., by a statistical analysis of the individual images recorded in phase 1) in a subsequent further phase 2. As soon as the markers have been successfully identified and localized, a third phase 3 is started. In this subsequent phase 3, the current individual image is continuously sent to the algorithm (e.g., during the ongoing recording), and the algorithm calculates, based on the result of phase 2, the coordinates of the markers, and hence the stent, in this current individual image to be displayed. Finally, all subsequently recorded individual images are spatially registered directly or indirectly via the identified and localized markers on the first individual image from phase 3 and time averaging (e.g., floating or recursive averaging) of the individual images registered to one another is performed.

As a result of the registration of the individual images to one another, averaging is performed using the image points representing the same object, namely the stent as a medical component and the marker pairs as markers and the parts of the patient (e.g., vessels). It is also additionally possible to optimize the section of the displayed image (e.g., the so-called windowing of the image), and to perform edge enhancement for better visibility of the stent. The result is a motion-stabilized scene relative to the marker pair, and hence the stent, in the environment of the marker pair with enhanced image quality. However, image parts at a greater distance to the marker pair are less sharp with this method. Unlike the method described above, this method provides images in real time so that the physician receives immediate optical feedback on an action (e.g., a displacement of the stent). The disadvantage is that parts of the image are blurred and the movements of the physician are depicted inversely because the movements are depicted relative to the stationary marker pair.

SUMMARY AND DESCRIPTION

The scope of the present invention is defined solely by the appended claims and is not affected to any degree by the statements within this summary.

One or more of the present embodiments may obviate one or more of the drawbacks or limitations in the related art. For example, the visibility with a medical component (e.g., a stent) is enhanced on an X-ray image.

The one or more of the present embodiments relate to a medical imaging X-ray device with a recording facility for recording at least two individual images of a series of images with a plurality of individual images of a body part of a patient, the location of a medical component in the body part is identified. The device also includes a computing facility for the localization of the medical component in the at least two recorded individual images and a display facility is provided for displaying a respective individual image of the series of images. One or more of the present embodiments also relates to a method for operating such a medical imaging X-ray device.

One or more of the present embodiments relate to a method for operating a medical imaging X-ray device. The method includes the recording of a first or earlier individual image (e.g., a so-called frame) of a series of images with a plurality of consecutive individual images of a body part of a patient. The series of images may also be designated an image sequence or film. The individual images may be two-dimensional images or three-dimensional recordings. An individual image may also be an X-ray recording. The location is identified of a medical component in the recorded body part visible on the individual image and the component is represented on the individual image additionally to the body part. The recording is performed by a recording facility of the X-ray device. The method also includes the localization of the medical component in the earlier or first individual image by a computing facility of the X-ray device. Methods known from the prior art may be used to detect, identify and localize the medical component fully automatically using previously known markers (e.g., the named marker pairs).

The method further includes the specification of a subregion (e.g., a so-called region-of-interest or ROI) of the earlier individual image or for the earlier individual image determined by the position (e.g., the location and/or the orientation) of the medical component localized in the earlier individual image and in which the localized medical component is represented. This procedure is performed by the computing facility. The subregion may be used to cut or select the image region of the individual image in which the medical component is localized. The method also includes the recording of a second or later individual image of the series of images and the localization of the medical component in the later individual image. This is followed by the later individual image being displayed by a display facility of the X-ray device. The later individual image is averaged exclusively region-specifically in an image region with the medical component (e.g. in a subregion or a region-of-interest with the medical component) with the subregion of the first earlier individual image.

Accordingly, the respective information is averaged with the image information for the subregion specified in the earlier individual image in the region or image region of the later individual image of the medical component. To this end, the two individual images are registered to one another (e.g., a clear spatial relationship is established between the image points of the respective individual images). Image points representing image information on identical real locations or position may be assigned to one another. This enables the specified subregion of the earlier individual image to be averaged (e.g., superimposed) in a locally precise way with the region of the medical component on the later individual image so that the contrast is enhanced without increasing image noise in the region of the medical component of the displayed later individual image.

Finally, a further \ repeated specification of the subregion, recording of a later individual image and displaying the later individual image may be performed, with the later individual image of a preceding repetition as an earlier individual image of a subsequent repetition. Hence, a continuous iterative method is provided with the subregion of the earlier or older individual image registered with the later individual image in order to combine the image information generated in the past by an averaging process with the currently generated image information for the later individual image in the region of the medical component or around the medical component and so to enhance the display.

One or more embodiments provide for weighting of the images in the averaging process in order to set a time horizon in the past beyond which the former image information disappears at a specified time point, as will be described below.

As described in the introduction, the registration may be performed using markers on the medical component. For example, as described in the introduction, initially, in a first phase 1, a sequence of individual images may be recorded, then, in a second phase 2, a suitable marker pair may be detected on the images. The described method may differs, because although the medical component may be localized for each individual image of the series of images using the marker pair (e.g., the position or location of the medical component may be determined) it may not be possible for all the individual images to be registered to one another. Instead, only one specifiable region-of-interest, the specified subregion about the markers (e.g., the marker pair) is cut from the last individual image and registered to the corresponding region (e.g., the subregion, or the ROI) of the respective displayed later individual image. It may now be possible, for time averaging (e.g., recursive time averaging) to be applied (e.g., exclusively within the respective region around the medical component). It may be necessary to rotate the subregion of the earlier individual image so that the medical component (e.g., the marker) has the correct alignment and the averaging may be performed in a locally precise manner and be included in an enhanced display. If there are corresponding markers suitable for direct detection, identification and/or localization, it is possible to dispense with the first phase 1 and the further phase 2, and to display the series of images with the individual images directly from the second individual image with an enhanced region around the medical component.

Due to the averaging over the respective subregions or regions with the medical component, an effective recording time is enlarged locally such that, without changing the dose in the region of the medical component, the contrast is intensified without increasing the noise at the same time. This enhances the visibility of the medical component on the X-ray image or the X-ray recording. However, because the averaging is performed exclusively in a limited region of the later individual image around the medical component, averaging-induced blurring is prevented of image parts of the displayed recording of the displayed later individual image outside the region around the medical component, which may account for a large part of the individual image. Moreover, in the display over the respective displacement of the subregion during the registration, it is also possible in a simple way to achieve a display with instrument motions that are not inverted because the marker pair, and hence the medical component, may be displaced in the series of images relative to a boundary of the image and not fixed in position as in the prior art.

Another embodiment provides that the medical component is a vessel support device, known as a stent or a dilation balloon. Both these medical components may be provided with markers that are identifiable on an X-ray image (e.g., automatically). For example, it is also possible for a geometric relationship and a spacing to be specified for the markers such that the markers are particularly easy to identify on an X-ray image, and consequently a position of the medical component may be determined in the individual image automatically.

In the case of a stent, during a cardiologic intervention, the beating of the heart results in a large movement between individual images such that, without corresponding averaging such as that described here, visibility of the stent is restricted. The same applies analogously to a dilation balloon during a cardiologic intervention.

Another embodiment provides that the subregion is specified by a size and in a shape as a function of the size and/or orientation of the localized medical component. For example, the subregion may be specified to only include image points of the corresponding individual image that are not located further than a specified maximum distance from the medical component.

Thus, visibility of the medical component is enhanced and the largest possible residual region of the individual image is unaffected by the statistical averaging and may be displayed with maximum/increased image sharpness. This facilitates the orientation of an observer of the individual image in the body part so that enhanced visibility of the medical component is combined with a best possible full overview.

A further embodiment provides that the subregion has a rectangular (e.g., square), a circular or an elliptical shape. The edge length and/or the radius or the radii may be specified as a function of the size of the medical component. A minimum or maximum size for the subregion may be specified in order (e.g., in the case of a required rotation of the subregion) not to go beyond a margin of the individual image or the series of images, and thus producing undefined image information and artifacts in the displayed individual image during the averaging.

The specified shape (e.g., and the specified size of the subregion) avoids irritation on the part of an observer, such as irritation arising as a result of artifacts in the case of subregions that vary in shape and or size during the series of images. Moreover, with circular and square subregions, it is also easy to achieve a corresponding rotation of the subregion, which may become necessary as a result of a rotation of the medical component.

Another embodiment provides that, during the display, the region of the displayed individual image in which the individual image is averaged with the subregion blends smoothly continuously into the rest of the displayed individual image. For example, distance-dependent alpha blending (e.g., superimposition dependent upon the distance to the medical component) is provided.

Thus, a slow transition between the enhanced region of the displayed individual image is achieved due to the averaging and the rest of the displayed individual image (e.g., with which the edges of the subregion are not clearly visible and are hence likewise depicted in a less disruptive manner).

Another embodiment provides that, during the display, the region of the displayed individual image in which the individual image is averaged with the subregion is separated from the rest of the individual image by a sharp boundary. For example, the edge may be visibly accentuated by additional marking.

Thus, the course of the edges of the enhanced region of the displayed individual image is clearly indicated and hence that, inside these boundaries, the image processing is different from image processing in the rest of the displayed individual image.

A further embodiment provides that the region of the medical component of the displayed individual image corresponds to the specified subregion or is this subregion. Hence, the subregion specified for the respective earlier individual image is only specified one single time (e.g., for the very first earlier individual image) and then remains the same with respect to shape and size and relative orientation to the medical component.

Thus, artifacts that occur precisely at the boundaries between the region of the medical component on the later individual image and the rest of the subregion may occur in the same location relative to the medical component, thus minimizing visual irritation for the observer.

A further embodiment provides that the displayed individual image in the region of the medical component is averaged recursively with the subregion of the earlier individual image. Therefore, the region is averaged using a recursion rule. For example, this enables the specification of a weighting ratio between the earlier and the later individual image, determining the above-explained time horizon for averaging in the past. Here, the greater the weighting of the later (e.g., more recent) individual image compared to the earlier (e.g., older) individual image, the more quickly former image information is no longer taken into account in the displayed individual image and is hence forgotten.

One or more embodiments provides that an item of image information (e.g., the intensity distribution) $ROI_t$ of the region with the medical component is defined in the later individual image by the equation 1 below:

$$ROI_t = \left(1 - \frac{1}{k}\right) RoTr\{ROI_{t-1}\} + \frac{1}{k} ROI_t. \qquad \text{Eq. 1}$$

where $ROI_{t-1}$ is the corresponding item of image information in the specified subregion of the earlier individual image. Initially, no averaging is performed for the first image with the image information $ROI_1$. The parameter k represents weighting of the earlier and later individual image during averaging (e.g., degree of the averaging). The function ROTR {x} describes a rotation and/or translation of the image information x (e.g., which may be required in order to align the respective subregion of the earlier individual image with the region of the medical component in the later individual image). The parameter k is also used to set the strength of the time filtering.

It is also provided that for one or more further image processing acts to be carried out to enhance visibility (e.g., edge enhancement and/or reduction of a window width, such as of the subregion or the region-of-interest). Thus, an improvement function or enhancement function E{x} is additionally applied to the image information ROI to enhance contrast and sharpness for the medical component (e.g., optionally additionally to adjust the brightness in the region around the medical component to the brightness of the rest of the displayed individual image). Thus, equation 2 applies:

$$ROI_t = E\left\{\left(1 - \frac{1}{k}\right) * RoTr\{ROI_{t-1}\} + \frac{1}{k} * ROI_t\right\}. \qquad \text{Eq. 2}$$

The recursive averaging or filtering provided has been found to be effective (e.g., precisely the strength of the time filtering). For example, the weighting of the averaging is an important parameter for achieving optimum visibility of the medical component.

One or more embodiments provide a medical imaging X-ray device with a recording facility for recording at least two individual images of a series of images with a plurality of individual images of a body part of a patient. The location of a medical component in the body part is identified, and a computing facility is provided for localizing the medical component in the at least two recorded individual images and with a display facility for displaying a respective individual image of the series of images or an item of image information obtained from these two individual images.

The computing facility may be configured to specify a subregion of an earlier individual image, with the subregion being determined by the position of the medical component localized in the earlier individual image. The localized medical component is represented and averaged or superimposed with a later individual image exclusively region-specifically in the (image-)region of the medical component with the subregion of the earlier individual image. A respective use of the later individual image of the earlier repetition as an earlier individual image of a later repetition with the corresponding localization and specification of the subregion causes the averaging to take place iteratively.

The features and feature combinations mentioned above in the description and the features and feature combinations mentioned below in the description of the figures and/or shown in the figures alone are usable not only in the respectively specified combination but also in other combinations or alone without departing from the scope of the invention. Hence, embodiments that are not explicitly shown or explained in the figures but are derived from and may be generated by separate feature combinations from the explained embodiments may also be considered to be disclosed. Hence, embodiments and feature combinations that do not have all the features of an originally formulated independent claim are also to be considered to be disclosed. Moreover, embodiments and feature combinations (e.g., from the above-described embodiments) that extend beyond or deviate from the feature combinations described in the back-references in the claims may also be considered to be disclosed.

DETAILED DESCRIPTION

Figure 1:
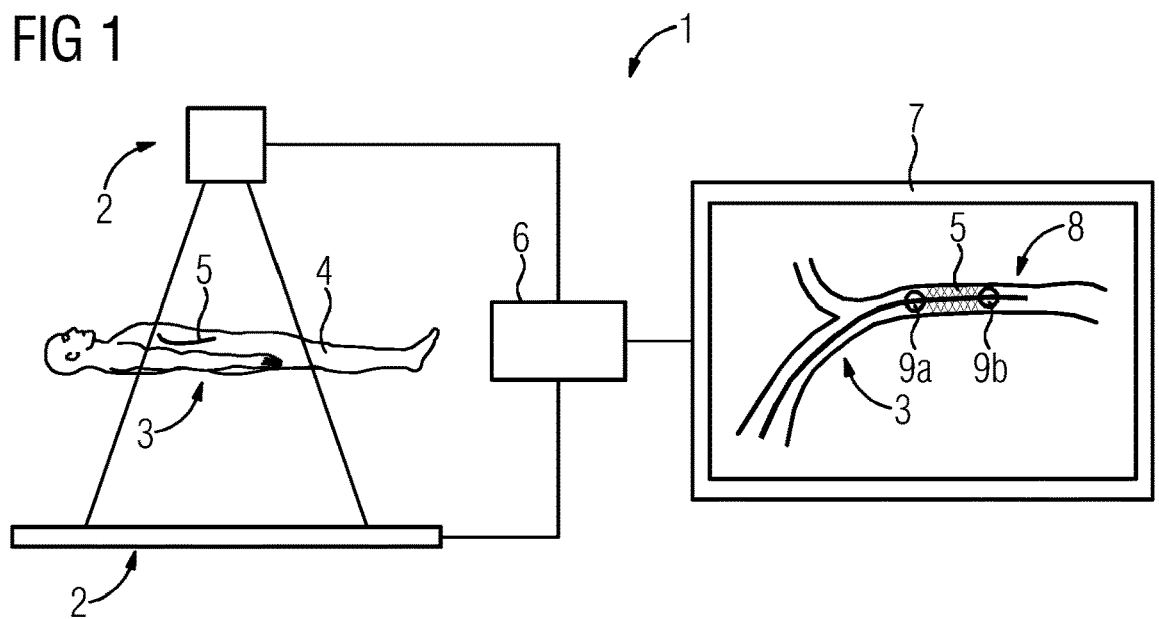
FIG. 1 illustrates an exemplary embodiment of a medical imaging X-ray device.

FIG. 1 depicts an exemplary embodiment of a medical imaging X-ray device. The medical imaging X-ray device 1 includes a recording facility 2 for recording at least two individual images of a series of images including a plurality of individual images of a body part 3 of a patient 4. The location of a medical component 5 in the body part 3 is identified in the images.

The X-ray device 1 further includes a computing facility 6 for localizing the medical component 5 in an X-ray recording (e.g., the recorded individual images). The X-ray device 1 further includes a display facility 7 for displaying a respective individual image 8 of the series of images.

The computing capacity 6 is configured for the repeated specification of a subregion of an earlier individual image, determined by the position of the medical component 5 localized in the earlier individual image and in which the localized medical component 5 is represented. The computing facility 6 is further configured to average a later displayed individual image 8 exclusively region-specifically in the region of the medical component 5 with the subregion of the earlier individual image. The respective use of the later individual image 8 of an earlier repetition with the corresponding localization and specification of the subregion as an earlier individual image of later repetition causes the averaging to take place iteratively.

As depicted, a blood vessel is depicted as a body part 3 on the individual image 8 displayed on the display facility 7. The medical component 5 (e.g., a stent) is introduced into the blood vessel. The stent includes two markers 9A, 9B arranged on the ends of the stent, enabling automatic localization of the medical component 5.

Figure 2:
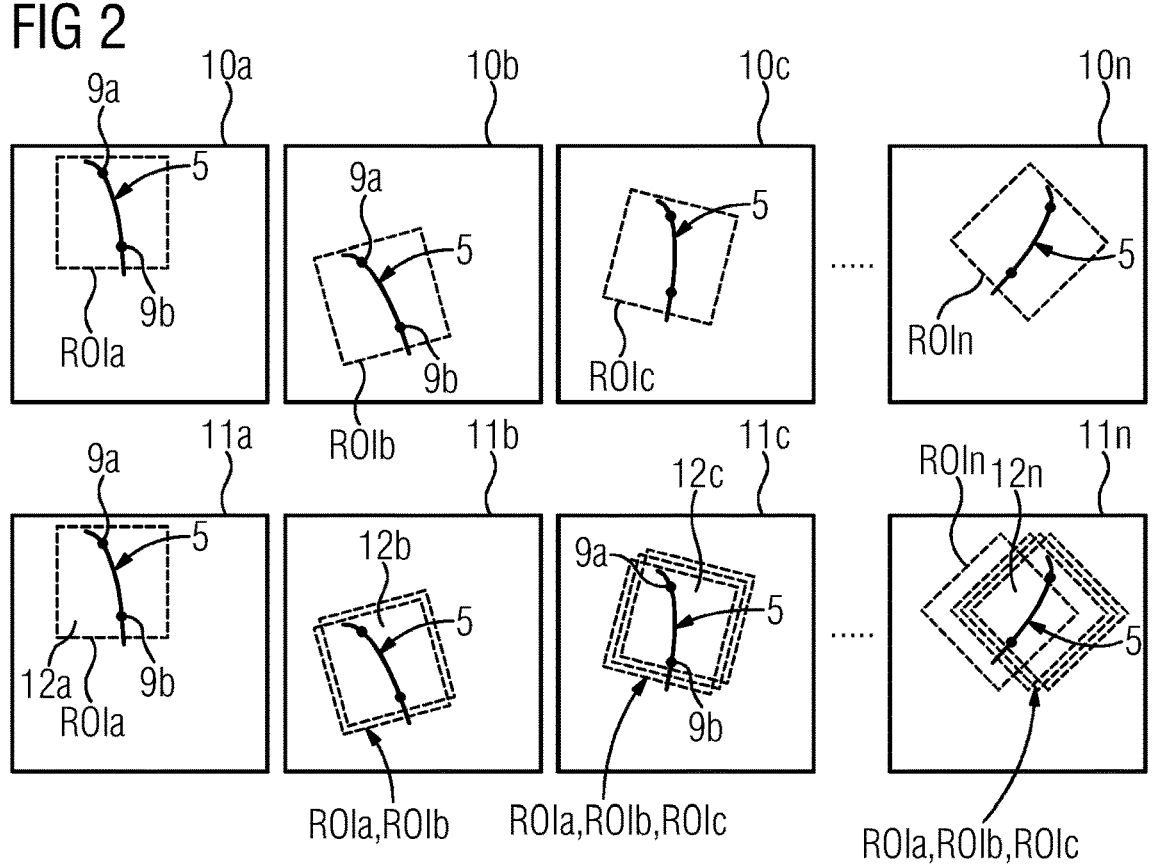
FIG. 2 illustrates an exemplary series of images with a sequence of individual images in that a respective subregion is specified.

FIG. 2 depicts individual images used to describe an exemplary embodiment of the method. A first upper sequence depicts recorded individual images 10a to 10n. For example, the individual image 10n is e.g. the last individual image of a series of images of X-ray recordings with a plurality of individual images. Herein, the medical component 5, e.g. a stent, is depicted in each of the individual images 10a to 10n. Also depicted are two respective markers 9A, 9B, that may be used for the automatic detection and localization of the medical component 5.

Following the recording of the corresponding individual image 10a to 10n by the recording facility 2, it is provided that the medical component 5 may be localized automatically in each individual image 10a to 10n by the computing facility 6 (e.g., depicted in FIG. 1). The computing facility 6 may specify a respective subregion ROIa to ROIn for each individual image 10a to 10n. The subregion is determined by the position (e.g., the location and orientation) of the medical component 5 localized in the assigned individual image 10a to 10n in each case, and may be adjusted to the size of the medical component 5 to be localized. The medical component 5 is represented on or in the subregion ROIa to ROIn. In the example shown, the respective subregion ROIa to ROIn is square-shaped.

A second lower sequence in FIG. 2 depicts a corresponding sequence of the displayed individual images 11a to 11n corresponding to the first sequence of the recorded individual images 10a to 10n. In lower sequence of images, the respective individual image 11a to 11n is averaged (e.g., superimposed) with the image information for the subregions ROIa to ROIn of the recorded individual images 10a to 10n in a respective region 12a to 12n around the medical component 5.

For example, in the first displayed individual image 11a, the region 12a only contains the image information for the subregion ROIa or the region 12a. In the second displayed individual image 11b, the image region 12b around the medical component 5 now contains the averaged image information for the subregions ROIa, ROIb of the first two recorded individual images 10a, 10b (e.g., the image region 12b averaged with the subregion ROIa). In the third displayed individual image 11c, the image region 12c around the medical component 5 contains the averaged image information for the subregions ROIa, ROIb, ROIc of the first three recorded individual images 10a, 10b, 10c (e.g., the image region 12c averaged with the subregions ROIa and ROIb). Finally, in the image region 12n of the n-th displayed individual image 11n, the image information for the n subregions ROIa, ROIb, ... ROIn of the recorded individual images 10a, 10b, ... 10n is averaged.

There may not be yet be any averaging for the first displayed individual image 11a for an iterative method, thus the displayed individual image 11a may be identical to the recorded individual image 10a.

If an earlier individual image 10a and a later individual image 10b are then recorded, the later individual image 10b as a displayed individual image 11b is averaged region-specifically in the region 12b with the subregion ROIa. Accordingly, the image information is averaged in the region 12b including of the subregion ROIa in the earlier individual image 10a, and because the subregion is specified the same for all recorded individual images 10a to 10n, the subregion ROIb (e.g., specified as such in the next iteration act).

If a third individual image 10c is now recorded, the displayed individual image 11c is averaged in the region 12c around the medical component 5 with the subregion 12b of the displayed previous individual image 11b. Because the region overlaps with the region 12b (e.g., even congruent therewith), the image information for the subregion 12a also blends into the averaging so that, in addition to the image information for the region 12, the image information for the subregions 12a and 12b is also displayed in the individual image 11c.

Accordingly, the n-th individual image 11n contains the image information for all the subregions 12a to 12(n−1). Hence, an averaging process over all these items of image information and the image information for the region 12n of the recorded n-ten individual image 10n achieves enhanced visibility of the medical component.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a medical imaging X-ray device, the method comprising:
    recording an earlier individual image of a series of images of a body part of a patient by a recording facility of the X-ray device;
    localizing a medical component in the recorded earlier individual image by a computing facility of the X-ray device;
    specifying, by the computing facility, a subregion of the earlier individual image, the subregion determined by a position of the medical component localized in the earlier individual image and representing the localized medical component;
    recording a later individual image in the series of images and localizing the medical component in the later individual image;
    registering the subregion of the earlier individual image with the later individual image based on the localized medical component in the earlier individual image and the later individual image to provide an enhanced image, wherein the later individual image is averaged exclusively in a region of the later individual image having the medical component with the subregion of the earlier individual image, and wherein no averaging occurs outside of the region of the later individual image;
    displaying the enhanced image by a display facility of the X-ray device, wherein visibility of the medical component is enhanced within the region of the later individual image and blurring of the enhanced image is avoided outside of the region of the later individual image, and wherein the region of the later individual image where the later individual image is averaged with the subregion of the earlier individual image blends smoothly into the rest of the enhanced image; and
    repeating, with the displayed enhanced image as the earlier individual image, the specifying of a new subregion, the recording of the later individual image and the displaying an enhanced image.

2. The method of claim 1, wherein the medical component is a stent or a dilation balloon, and
    wherein the stent or dilation balloon is provided with markers to be automatically identified on an X-ray image.

3. The method of claim 1, wherein the subregion of the earlier individual image is specified by a size and as a function of a size of the localized medical component.

4. The method of claim 1, wherein, the subregion of the earlier individual image has a rectangular, a square, a circular or an elliptical shape.

5. The method of claim 1, wherein the region of the medical component of the enhanced image corresponds to the subregion of the earlier individual image.

6. The method of claim 1, wherein the region of the medical component is averaged recursively with the subregion of the earlier individual image.

7. The method of claim 6, wherein an item of image information $ROI_t$ of the region of the medical component is defined by:

$$ROI_t = \left(1 - \frac{1}{k}\right) RoTr\{ROI_{t-1}\} + \frac{1}{k} ROI_t$$

with $ROI_{t-1}$ defined as image information for the subregion,
    wherein the parameter k determines a weighting of the averaging and $RoTr\{\ \}$ represents a rotation, a translation, or the rotation and the translation.

8. A medical imaging X-ray device comprising:
    a recording facility for recording at least two individual images of a series of images of a body part of a patient;
    a computing facility for localizing a medical component in the at least two recorded individual images; and
    a display facility for displaying a respective individual image of the series of images,
    wherein the computing facility is configured for repeated specification of a subregion of an earlier individual image, the subregion determined by the position of the medical component localized in the earlier individual image representing the localized medical component,
    wherein the computing facility is configured to register the subregion of the earlier individual image with a later individual image based on the localized medical component in the earlier individual image and the later individual image to provide an enhanced image, wherein the later individual image is averaged exclusively in a region of the later individual image having the medical component with the subregion of the earlier individual image, and wherein no averaging occurs outside of the region of the later individual image, wherein the display facility is configured to display the enhanced image such that visibility of the medical component is enhanced within the region of the later individual image and blurring of the enhanced image is avoided outside of the region of the later individual image, and wherein the region of the later individual image where the later individual image is averaged with the subregion of the earlier individual image blends smoothly into the rest of the enhanced image, and wherein a respective use of the displayed enhanced image of an earlier repetition as an earlier individual image of a later repetition causes the averaging to take place iteratively.

9. The method of claim 1, wherein the region of the later individual image where the later individual image is averaged with the subregion of the earlier individual image blends smoothly into the rest of the enhanced image via distance-dependent alpha blending.

10. The method of claim 9, wherein the distance-dependent alpha blending comprises a superimposition dependent upon a distance to the medical component.

\* \* \* \* \*